(12) United States Patent
Stock

(10) Patent No.: US 6,289,718 B1
(45) Date of Patent: Sep. 18, 2001

(54) ARRANGEMENT FOR DETECTING A GASEOUS COMPONENT IN A GAS FLOW

(75) Inventor: Burkhard Stock, Lübeck (DE)

(73) Assignee: Dräger Sicherheitstechnik GmbH, Lübeck (DE)

( * ) Notice: Subject to any disclaimer, the term of this patent is extended or adjusted under 35 U.S.C. 154(b) by 0 days.

(21) Appl. No.: 09/345,412

(22) Filed: Jul. 1, 1999

(30) Foreign Application Priority Data

Jul. 29, 1998 (DE) .................................. 198 33 991

(51) Int. Cl.$^7$ .................................................. G01N 25/00
(52) U.S. Cl. ............................................. 73/23.2; 73/1.06
(58) Field of Search ...................................... 73/1.06, 23.2

(56) References Cited

U.S. PATENT DOCUMENTS

| | | | |
|---|---|---|---|
| 4,090,078 | * 5/1978 | Heim ................................. 250/343 |
| 4,300,385 | * 11/1981 | Albarda ................................. 73/23 |
| 4,316,380 | * 2/1982 | Heim et al. ........................... 73/23 |
| 4,833,909 | * 5/1989 | Matthiessen .......................... 73/23 |
| 5,069,220 | 12/1991 | Casparie et al. . | |
| 5,321,972 | * 6/1994 | Stock .................................... 73/23.2 |
| 5,369,977 | * 12/1994 | Rhodes et al. ........................ 73/23.3 |
| 5,398,695 | 3/1995 | Anderson et al. . | |
| 5,400,637 | 3/1995 | Forrester . | |
| 5,443,794 | * 8/1995 | Williams ................................ 422/84 |
| 5,496,740 | * 3/1996 | Williams .............................. 436/132 |
| 5,524,084 | * 6/1996 | Wang et al. ......................... 364/510 |
| 5,739,412 | * 4/1998 | Stock et al. ........................... 73/23.3 |
| 5,770,793 | * 6/1998 | Stock ................................... 73/23.21 |
| 5,866,794 | * 2/1999 | Stock ..................................... 73/1.06 |
| 6,150,177 | * 11/2000 | Stock ..................................... 436/132 |
| 6,167,746 | * 1/2001 | Gammenthaler .................... 73/19.01 |

* cited by examiner

Primary Examiner—Hezron Williams
Assistant Examiner—Charles D. Garber
(74) Attorney, Agent, or Firm—Walter Ottesen

(57) ABSTRACT

The invention is directed to an arrangement for detecting a gaseous component in a gas flow which reaches a measuring chamber (4) via a sample intake line (3). The arrangement includes a flow throttle (8) in the sample intake line (3) and has a pressure sensor (9) for detecting the pressure at the inflow end of the flow throttle (8). The pressure sensor (9) can also be used to measure the ambient pressure. A flow detector (10) for generating a zero-flow signal is provided at a position along the sample intake line (3).

3 Claims, 1 Drawing Sheet

ARRANGEMENT FOR DETECTING A GASEOUS COMPONENT IN A GAS FLOW

BACKGROUND OF THE INVENTION

U.S. Pat. No. 4,833,909 discloses an apparatus for detecting a gaseous componet in air. The apparatus includes a measuring chamber through which a throughflow can take place from a gas inlet to a gas outlet. The gas sample to be investigated is guided through a sample intake line to the gas inlet of the measuring chamber. A pressure is built up in the sample intake line at the inflow end by means of a throttle and this pressure is detected by a pressure sensor. The pressure measurement signal supplied by the pressure sensor is an index for the velocity of the gas flow within the gas sample intake line. A value proportional to the gas volume can be determined by a time integration of the pressure measurement signal.

Arrangements are known wherein a measurement value is needed for calibration purposes and this measurement value is proportional to the ambient pressure. Test gases from pressure cylinders are used for the calibration and these test gases are fed into the measuring apparatus to be checked. Generally, the test gas concentration is indicated in ppm or volume percent on the pressure cylinders and the test gas concentration is thereby independent of pressure. The concentration indication on the pressure cylinders and the value supplied by the measurement apparatus are only coincident for the ambient pressure at which the measuring apparatus was adjusted with this test gas. With changes of the ambient pressure, a difference arises which must be corrected. An arrangement for correcting the ambient pressure influence is disclosed in U.S. Pat. No. 5,400,637.

SUMMARY OF THE INVENTION

It is an object of the invention to improve an arrangement of the kind described above so that a sample intake line can be detected wherein there is no flow.

The arrangement of the invention is for detecting a gaseous component in a gas flow. The arrangement includes: a measuring chamber wherein the gaseous component of the gas flow is measured; a sample intake line for conducting the gas flow into the measuring chamber; a flow throttle mounted in the intake line; a pressure sensor for detecting the pressure in the sample intake line upstream of the flow throttle and for generating a pressure measurement signal indicative of the pressure in the sample intake line; and, a flow detector mounted along the sample intake line for generating a zero signal when there is a nonflow in the sample intake pipe and a nonzero signal when there is a gas flow in the sample intake line.

The advantage of the invention is essentially that a static gas flow can be detected with the flow detector mounted in the sample intake line and the pressure sensor, which is present, can be used to detect the velocity of the gas flow within the sample intake line as well as to determine the absolute ambient pressure.

The flow detector is advantageously configured as a hot wire anemometer. The cooling of the hot wire is an index for the presence of a gas flow. As an alternative to a hot wire anemometer, a measuring system can be used wherein a flexible tongue is deflected which is located in the gas flow.

It is especially advantageous to use a switching device which is operatively connected to the flow detector. With this switching device, a switching connection to a first evaluation path is established when a flow zero signal is present. The evaluation path forms, from the pressure measurement signal, a first pressure signal, which is proportional to the ambient pressure. Insofar as the flow detector supplies a value other than zero, a switching connection to a second evaluation path is established by the switchover device. The second evaluation path then determines, from the pressure measurement signal, a quantity proportional to the velocity of the gas flow in the sample intake line. The switchover device and the evaluation paths can be configured as discrete components or even in the form of software modules in a microprocessor.

The arrangement according to the invention is especially advantageous as a breath alcohol measuring apparatus wherein a calibration with a test gas mixture must be carried out at specific intervals.

BRIEF DESCRIPTION OF THE DRAWING

The invention will now be described with respect to the single FIGURE (FIG. 1) of the drawing which is a schematic of an embodiment of the measuring arrangement according to the invention.

DESCRIPTION OF THE PREFERRED EMBODIMENTS OF THE INVENTION

Figure 1:
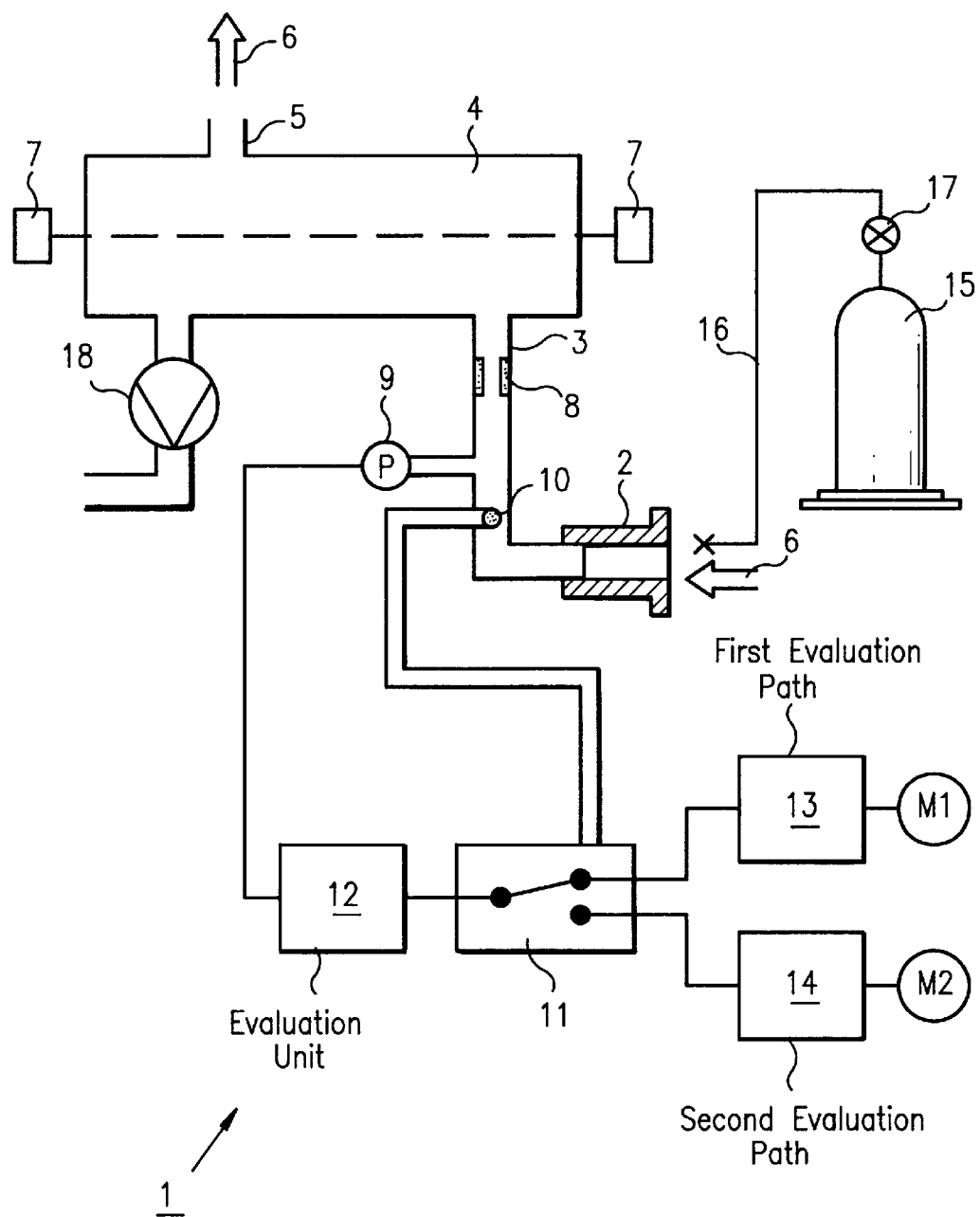

FIG. 1 shows a measuring apparatus 1 for determining the breath alcohol concentration. A subject person (not shown) to be tested exhales or blows the gas sample to be analyzed into a measuring chamber 4 via a mouthpiece 2 and a sample intake line 3. The measuring chamber 4 has a gas outlet 5 open to the ambient. The throughflow direction of the sample intake line 3 and the measuring chamber 4 is shown in FIG. 1 by the arrow 6.

An infrared measuring apparatus 7 is disposed on the measuring chamber 4 and analyzes the gas sample blown in. A pressure is built up in the sample intake line 3 because of the flow throttle 8 and this pressure is detected by a pressure sensor 9. A flow detector 10 is disposed in the sample intake line 3 in flow direction forward of the pressure sensor 9. The flow detector 10 is configured as a hot wire anemometer and outputs a control signal in the non-flow state of the sample intake line 3. The control signal is in the form of a flow zero signal and is outputted to a changeover switch 11. The changeover switch 11 is connected via an evaluation unit 12 to the pressure sensor 9.

The evaluation unit 12 converts the measured pressure into an electrical pressure measurement signal. Depending upon the switching position of the changeover switch 11, there is either a signal flow from the evaluation unit 12 to a first evaluation path 13 or the evaluation unit 12 is connected to a second evaluation path 14. In the first evaluation path 13, a first measurement signal M1 is formed from the pressure measurement signal and is proportional to the ambient pressure; whereas, the second evaluation path 14 supplies from the pressure measurement signal a second measurement signal M2 which is proportional to the gas flow in the sample intake line 3. FIG. 1 shows the position of the changeover switch 11 for a probe sample line 3 in which there is no flow and wherein the evaluation unit 12 is connected to the first evaluation path 13.

The calibration of the measuring arrangement 1 is carried out as explained below.

A pressure cylinder 15 is filled with test gas and is cut off by a valve 17. The pressure cylinder 15 is connected via a tube 16 to the mouthpiece 2. The measuring chamber 4 is flushed with the test gas by opening the valve 17. The flow detector 10 registers a gas flow in the sample intake line 3 and the evaluation unit 12 is connected to the second evaluation path 14 via the changeover switch 11. The measurement signal M2 is determined via the second evaluation path 14 and is an index for the adequate flushing or purging of the measurement chamber 4 with the test gas. The infrared measuring device 7 determines the gas component of the test gas to be detected. After the valve 17 is switched into the closed position, the flow detector 10 registers a sample intake line 3 through which there is no flow and the changeover switch 11 is switched into the position shown in FIG. 1 by the zero-flow signal generated by the flow detector 10. Now, a measurement of the ambient pressure is possible with the pressure sensor 9. The pressure compensation of the measuring chamber 4 and of the sample intake line 3 to the ambient takes place via the gas outlet 5. With a pump 18, the measuring chamber 4 can thereafter be flushed with ambient air and thereby be prepared for a measurement of a test person.

It is understood that the foregoing description is that of the preferred embodiments of the invention and that various changes and modifications may be made thereto without departing from the spirit and scope of the invention as defined in the appended claims.

What is claimed is:

1. An arrangement for detecting a gaseous component in a gas flow, the arrangement comprising:

a measuring chamber wherein the gaseous component of said gas flow is measured;

a sample intake line for conducting said gas flow into said measuring chamber;

a flow throttle mounted in said intake line;

a pressure sensor for detecting the pressure in said sample intake line upstream of said flow throttle and for generating a pressure measurement signal indicative of said pressure in said sample intake line;

a flow detector mounted along said sample intake line for generating a zero signal when there is a nonflow in said sample intake pipe and a nonzero signal when there is a gas flow in said sample intake line;

a first evaluation path for forming a first measurement signal proportional to the ambient pressure in response to said pressure measurement signal supplied by said pressure sensor; and, changeover switching means operatively connected to said flow detector for connecting said pressure sensor to said first evaluation path in response to said zero signal whereby said first measurement signal is formed by said first evaluation path.

2. The arrangement of claim 1, wherein said flow detector is a hot-wire anemometer.

3. The arrangement of claim 1, further comprising:

a second evaluation path forming a second measurement signal proportional to said gas flow in said sample intake line from said pressure measurement signal; and, said changeover switching means being configured to switch into a first position to connect said pressure sensor to said first evaluation path in response to said zero signal whereby said first measurement signal is formed and into a second position to connect said pressure sensor to said second evaluation path in response to said nonzero signal of said flow detector.

* * * * *

UNITED STATES PATENT AND TRADEMARK OFFICE
CERTIFICATE OF CORRECTION

PATENT NO. : 6,289,718 B1
DATED : September 18, 2001
INVENTOR(S) : Burkhard Stock It is certified that error appears in the above-identified patent and that said Letters Patent is hereby corrected as shown below:

Column 1,
Line 7, delete "componet" and substitute -- component -- therefor.
Line 51, delete "pipe" and substitute -- line -- therefor.

Column 4,
Line 7, delete "pipe" and substitute -- line -- therefor.

Signed and Sealed this

Thirtieth Day of April, 2002

Attest:

JAMES E. ROGAN
Attesting Officer
Director of the United States Patent and Trademark Office